US006988827B2

(12) United States Patent
Mueller

(10) Patent No.: US 6,988,827 B2
(45) Date of Patent: Jan. 24, 2006

(54) COOLING SYSTEM AND METHOD TO COOL A GANTRY

(75) Inventor: Hans-Juergen Mueller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 13 days.

(21) Appl. No.: 10/772,754

(22) Filed: Feb. 5, 2004

(65) Prior Publication Data

US 2004/0228450 A1     Nov. 18, 2004

(30) Foreign Application Priority Data

Feb. 5, 2003   (DE) .............................. 103 04 661

(51) Int. Cl.
*H01J 35/10*   (2006.01)
(52) U.S. Cl. .................................... 378/199
(58) Field of Classification Search ............. 378/4, 378/15, 199
See application file for complete search history.

(56) References Cited

U.S. PATENT DOCUMENTS

| 4,115,697 A * | 9/1978 | Hounsfield et al. ........... 378/15 |
| 6,412,979 B1 | 7/2002 | Hell et al. .................. 378/200 |
| 6,709,156 B1 | 3/2004 | Hell et al. .................. 378/199 |
| 2004/0202287 A1 * | 10/2004 | Muller ....................... 378/199 |

FOREIGN PATENT DOCUMENTS

| DE | 198 45 756 | 4/2000 |
| DE | 199 45 413 | 4/2001 |

* cited by examiner

*Primary Examiner*—David V. Bruce
*Assistant Examiner*—Courtney Thomas
(74) *Attorney, Agent, or Firm*—Schiff Hardin LLP

(57) ABSTRACT

A cooling system for a gantry of a computer tomography system which has a gantry supporting an x-ray source being positioned in a gantry housing and being rotatable around a rotation axis, the gantry housing being positioned by at least one bearing on a stationary part of the computer housing so that it can be moved relative to the housing. The cooling system comprises a cooling gas supply arrangement or device directing a cooling gas flow in the region of at least one bearing between the stationary part and the gantry housing.

22 Claims, 4 Drawing Sheets

COOLING SYSTEM AND METHOD TO COOL A GANTRY

BACKGROUND OF THE INVENTION

The invention concerns a cooling system for a gantry and a computer tomography system with an x-ray source, positioned in a gantry housing and rotatable around a rotation axis, in which the gantry housing is positioned at a stationary part of the computer tomography system so that it can be moved, in particular pivoted, by means of at least one bearing. Moreover, the invention concerns a corresponding method to cool such a gantry.

In computer tomography systems, three-dimensional slice images of the inside of an examination subject are generated with the aid of an x-ray method. For this, by means of a scanning unit—in general called a gantry—which comprises an x-ray source normally rotating around the acquisition subject and an image acquisition system, two-dimensional x-ray slice images are generated from which a three-dimensional slice image is reconstructed. The gantry is typically located in a gantry housing which is annularly arranged around an examination subject acquisition space. In computer tomography systems of the previously cited type, a tilting of the image plane relative to the examination subject can additionally be achieved by pivoting the gantry housing or, respectively, the gantry, in order to achieve, for example, a slice direction parallel to the subject surface. In this manner, for example, arbitrary coronary slices can be created.

A basic problem in all x-ray systems is that 99% of the electrical energy used in the generation of the x-ray radiation in the x-ray source is transduced into heat energy. This heat accumulating in the operation of the x-ray source must be dissipated from the x-ray source in order to be able to operate the x-ray source over a longer span of time without an overheating of the source. This is in particular necessary when high x-ray densities are required. In computer tomography systems of the previously cited type, it additionally aggravates matters that the x-ray source continuously rotates in the gantry housing around the examination subject acquisition space during a radiological exposure. Due to this continuous rotation movement, the extremely high temperatures and the narrowness of the inner space of the gantry housing, the dissipation of the heat accumulating in the operation of the x-ray system proves to be complicated and problematic.

The cooling systems used until now in such computer tomography systems are for the most part formed of a plurality of heat exchangers that are installed inside the gantry housing. In order to dissipate the heat accumulating at the rotating x-ray source from the gantry and from the inside of the gantry housing as efficiently as possible, conventionally a heat exchanger is mounted in direct proximity to the x-ray source and rotating with it. This first heat exchanger dissipates the heat to the air surrounding the gantry in the gantry housing. The heated air around the gantry can, for example, by cooled by a second heat exchanger which dissipates the heat acquired from the air to a cooling system outside of the gantry housing. Allowed U.S. patent application Ser. No. 09/664,338, whose disclosure is incorporated herein by reference thereto and which claims priority from DE 199 45 413, shows a computer tomography system in which the second heat exchanger is arranged stationary in the gantry housing relative to the x-ray radiator. The heat acquired during the operation by the second heat exchanger is dissipated by coolant lines to a cooling system outside of the gantry housing. U.S. Pat. No. 6,412,979, whose disclosure is incorporated herein by reference thereto and which claims priority from DE 198 45 756, offers an alternative. In the computer tomography system shown there, the second heat exchanger is arranged in the gantry housing, rotating with the gantry. The dissipation of the heat ensues during the idle periods [downtimes; standstill periods] of the gantry between two measurements, in which the second heat exchanger is coupled by means of a rapid coupling with a water cooling circuit or loop arranged outside of the gantry housing.

It proves to be disadvantageous in the cited cooling systems that a plurality of precise mechanical and electrical components are necessary that, due to their function, tend to wear out and must be correspondingly maintained. A further disadvantage is that the gantry housing must be correspondingly, voluminously dimensioned, due to the size of the required heat exchanger. However, quite good cooling capacities can be achieved with the last described variant. However, it has a what is disadvantage which is that the cooling of the coolant is possible only given sufficient idle periods. Moreover, the pivotable realization of the gantry housing is hampered due to the necessary coupling to an external coolant circuit.

SUMMARY OF THE INVENTION

It is therefore the object of the invention to achieve a simply fashioned, cost-effective cooling system which requires little space in the gantry housing.

This object is achieved with a cooling system for a gantry of a computer tomography system, said gantry having an x-ray source and being positioned in a gantry housing for rotation around a rotational axis, the gantry housing being mounted by at least one bearing in a stationary part of the computer tomography system so that it can be pivoted on said at least one bearing, the cooling supply system including a cooling gas supply device for directing a cooling gas flow in the region of the at least one bearing between the stationary part and the gantry housing.

The object of the invention is also achieved by a method for cooling a gantry of a computer tomography system, which gantry has an x-ray source and is positioned in a gantry housing for rotation around a rotational axis and that the gantry housing is positioned by at least one bearing for pivoting in a stationary part of the computer tomography system, the method comprising directing a cooling gas flow between the stationary part and the gantry housing.

A cooling gas guide device is here inventively used to cool the gantry in order to direct the a cooling gas flow in the region of the bearing from the stationary part—typically also called a gantry foot—into the gantry housing and then from the gantry housing back into the gantry foot. For cost reasons, and for reasons of simplicity, simple air is preferably used as cooling gas in the majority of cases. In the following, therefore, the terms cooling gas and air are often used synonymously. However, the invention is not limited to a use of air as a cooling gas.

The inventive cooling system has the advantage that neither heat sinks that absorb and dissipate the waste heat of the components of the gantry, in particular of the x-ray source, from the gantry housing must necessarily be integrated into the gantry housing, nor that idle period or pauses of the gantry are necessary to dissipate the heat, since a cooling gas continuously flows from the gantry foot through the gantry housing and from the gantry housing back into the gantry foot, and this flow efficiently cools the components including the x-ray source which are located in the gantry housing.

In the presently common computer tomography systems, the gantry housing is mounted for pivoting around a pivot axis by means of two coaxial pivot bearings positioned in the gantry foot on opposite sides of the gantry housing.

The inventive cooling system is fashioned in such systems according to a first preferred embodiment, so that the cooling gas flows into the gantry housing in the region of one of the pivot bearings, flows through the gantry housing, and then flows back into the gantry foot in the region of the second pivot bearing.

This embodiment or variant of the invention lends itself to streaming or flowing the cooling gas in a closed circuit. The cooling gas is held internally in the gantry housing or, respectively, in a stationary part, so that no exchange ensues with the patient examination space. Such a structural shape is particularly preferable when a sterile environment is necessary.

In an alternative open system, the heated cooling gas can be exhausted or, respectively, dissipated through exhaust openings in the gantry foot of the computer tomography system. A particularly preferred embodiment or variant provides that the heated air is ducted outwards from the patient examination space via dissipation in order to prevent a stress of a climate system of the patient examination space. For this, corresponding dissipation tubes or hoses that are preferably connected to the gantry foot that, for example, are connected with a suitable exhaust air system of the examination space.

In a further open embodiment or variant of the invention, the gantry housing is designed so that the outer wall of the gantry housing itself comprises at least one exhaust opening. In this variant, the cooling gas is also directed out from the gantry foot in a bearing region in the gantry housing. However, the cooling gas here escapes directly from the exhaust opening of the gantry housing without first being directed back into the gantry foot. The exhaust openings can be one or more large openings. However, the housing is preferably perforated radially outwards in a specific region, that extends away from the examination subject. The cooling system in this embodiment is preferably fashioned so that the air flows into the gantry housing in the region of both pivot bearings. The cooling gas throughput is thereby increased.

In the previously specified exemplary embodiments with a closed cooling gas circuit, the inventive cooling system is preferably fashioned so that the air is sucked in from the patient examination space or from outside via a tube line system or hose system through at least one inflow opening in the stationary part. In order to prevent the components in the gantry housing from becoming contaminated by the sucked-in cooling air, at least one filter or something similar is preferably located in the cooling air flow in front of the gantry housing in order to filter out dust and other particles.

The streaming or flowing of the cooling gas into the gantry housing and/or back is preferably achieved by means of at least one blower arranged in the gantry foot. Such a blower is preferably located in the proximity of the bearing.

There are various possibilities for the cooling gas supply or, respectively, cooling gas drainage from the gantry foot into the gantry housing and back in the region of the bearing.

A variant or embodiment of the invention provides that the cooling gas flows through a flow-through opening running lengthwise through the bearing from the stationary part into the gantry housing and/or back. For this, the bearing is fashioned, for example, as a bearing ring or bearing tube. The clear opening cross-section of the bearing ring inner diameter or bearing tube inner diameter should be as large as possible so that the air exchange can occur largely unhindered.

In another preferred embodiment or variant, flow-through openings are located in the opposite-facing surfaces of the gantry housing arranged adjacent to the bearings and of the housing of the gantry foot. In this embodiment, the cooling gas throughput is increased via the increased area of the flow-through openings. In order to maintain the pressure of the cooling gas, the flow-through openings are sealed to the outside, so that no cooling gas can leak to the outside from the gap between gantry housing and the housing of the gantry foot. The possible shape, opening size and arrangement of the flow-through openings are optimally determined for each type or series of tomography systems, dependent on the housing geometry, the housing dimensions as well as the desired tilt angle.

Incidentally, a combination of both previously cited embodiments is possible, for example, an assembly in which flow-through openings are located within the bearing and in the housing surfaces near the respective bearing.

In order increase the effect of the cooling system, in the preferred exemplary embodiments of the invention additional heat exchangers are mounted in the stationary part. The heat exchangers cool the air, for example, before the entry into the gantry housing and/or after leaving the gantry housing before the discharge into the patient examination space, or in a closed circuit before a renewed flow-through from the gantry housing into the gantry foot. In an exemplary embodiment, the heat exchangers are preferably placed adjacent to the blowers. The heat exchangers can be connected to a cooling fluid, such as, for example, a simple cooling water.

The gantry housing can preferably be designed so that guide surfaces and/or guide channels are provided inside the gantry housing, and preferably extending radially inwards towards the gantry. The desired flow of the cooling gas in the gantry housing is thereby created. The conductive surfaces can also be arranged on the rotating part of the gantry.

In addition to the already-cited blowers in the region of the bearing, additional blowers can be installed in the stationary part in order to convey the flow into the gantry foot. This is in particular true for a system with a closed circuit.

The substantial advantage of the fashioning of the cooling system as a cooling gas supply system in the region of the bearings is that it is not necessary to install a plurality of heat exchangers in the gantry housing. The cooling system is thus a relatively simple and cost-effective system. Since no additional mechanical parts must be installed inside the gantry housing, on the one hand the production costs are already lower and, on the other hand, the maintenance costs of the entire system are reduced. Moreover, the cooling system also has the advantage that a cost-saving design of a smaller gantry housing is possible. An additional advantage of this cooling system is that the coupling of an external coolant pump to the outside of the gantry housing during the idle period pauses is not necessary. The pivotable realization of the gantry housing is thus simplified.

The inventive cooling system can be used in special designs, and also with particular advantage in a continuously rotating computer tomography device. Thus, the cooling system can be used in a computer tomography device which, for example, rotates uninterrupted during a working shift, during a workday or over a plurality of examinations. Given such an embodiment, the rotation of the scanning unit around the system axis can be effected uninterrupted from the beginning of the examination of a first examination subject until the end of a following examination of a second examination subject. "Uninterrupted" does not necessarily mean that the uninterrupted rotation is effected with constant rotation frequency. Rather, the rotation frequency of the scanning unit can advantageously be set differently dependent on the type of the desired examination, for example for an examination of the heart or of the abdomen of a patient. A correspondingly fashioned computer tomography device can in particular be fashioned so that the scanning unit then rotates with a preset rotation speed ("stand-by setting") in the event that no examination is directly occurring. This rotation speed is, for example, less than the rotation speeds available for the applications, or is in the range of the average value of the rotation speeds available for the applications, so that the change of the rotation speed is small given a new application in the middle of other applications. The span of time of the uninterrupted rotation can also extend over a week or longer. A continuously rotating computer tomography device has the advantage that time-intensive braking or starting intervals can be avoided, which up until now were necessary, for example for an always-necessary repositioning of the scanning unit before each new examination. Given a continuously rotating computer tomography device, the temperature stability and temperature homogeneity of the entire tomography device is additionally improved. This stability enables an execution of the cooling system in a simplified manner.

Moreover, the cooling system can also be used supplementary to already known cooling methods. The inventive air cooling can preferably also be used in order to cool the heat exchangers arranged on and rotating with the gantry, and thus to increase their efficiency.

In particular, a retrofitting of already existing computer tomography systems is also possible. For this, only one suitable arrangement of blowers in the gantry foot as well as inflow or, respectively, outflow openings in the gantry housing and/or in the housing of the gantry foot and/or in the bearings is necessary.

The invention is explained again in detail in the following exemplary embodiments, with reference to the attached Figures. Identical components are respectively provided with the same reference numbers in the various Figures.

DESCRIPTION OF THE PREFERRED EMBODIMENTS

Figure 1:
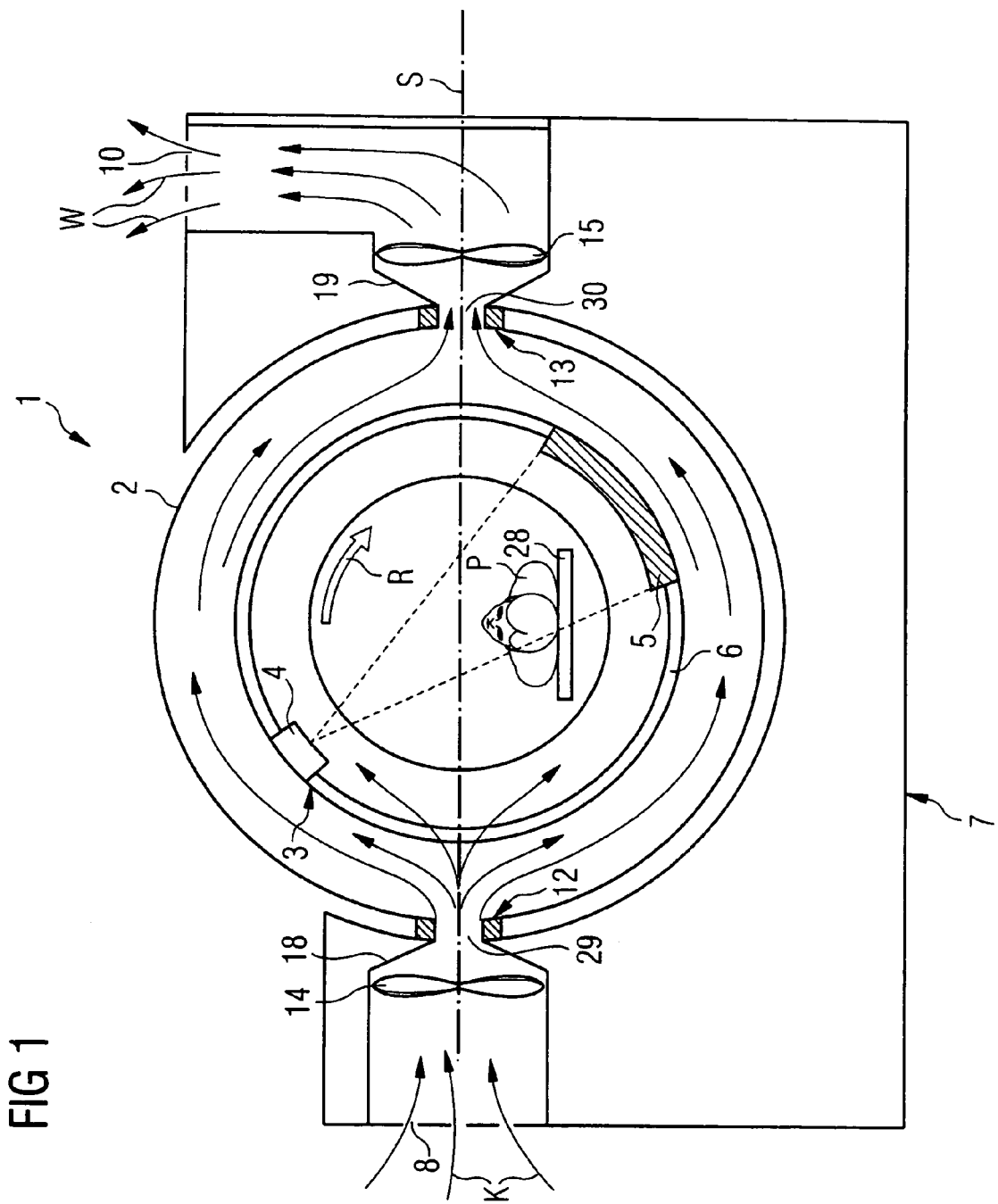
FIG. 1 is a schematic cross-sectional view of a computer tomography system with an inventive cooling system according to a first exemplary embodiment.

The principles of the present invention are particularly useful when incorporated in the cooling system illustrated in FIGS. 1–4.

The computer tomography system 1 shown in FIG. 1 comprises as a primary component a stationary part 7, which is called a gantry foot in the following and a gantry housing 2, movably positioned thereon, which is fashioned in an approximate torus shape, meaning as a "donut" and is movably mounted on the gantry foot 7. Located in the gantry housing 2 is a gantry 3 with a carrier ring 6, which is also called a drum. The gantry is mounted so that it can be rotated in the rotation direction of arrow R, and an x-ray source 4 and a detector 5 are arranged opposite one another on the gantry 7. In the operation of the computer tomograph 1, the drum 6 rotates around an examination subject or patient P positioned on a bed 28 in the examination space, so that a fan-shaped x-ray beam emitted by the x-ray source 4 penetrates the examination subject and impinges on the detector 5. A slice image of the inside of the patient P is thus acquired in a slice lying in the rotation plane of the drum 6.

The gantry housing 2 can be pivoted on a pivot axis S by means of two coaxial pivot bearings 12, 13, which are positioned on opposite sides of the gantry foot 7. A tilting of the slice image plane is achieved by pivoting the gantry housing 2, and the gantry 3, on the pivot axis S.

In the case of the exemplary embodiment shown in FIG. 1, a first blower 14 is arranged on one side of the gantry housing 2 in the region of the pivot bearing 12. The blower 14 effects the blowing of a cold air flow K into the gantry housing 2. The cold air flow K is drawn into the housing of the gantry foot 7 through inflow openings 8 and directed via a flow-through opening 29 in the bearing 12 into the gantry housing 2. The air heated in the gantry housing 2 is then exhausted again from the gantry housing 2 via a flow-through opening in the opposite pivot bearing 13 by means of a second blower 15 which is located on the opposite side of the gantry housing 2 in the gantry foot 7. The warm air flow W can subsequently escape through outflow openings 10 in the housing of the gantry foot 7. Since the diameters of the blowers 14, 15 do not correspond with the diameters of the flow-through openings 29, 30, the blowers 14 and 15 are connected to the openings 29 and 30 by funnel-shaped duct sections 18, 19.

Figure 2:
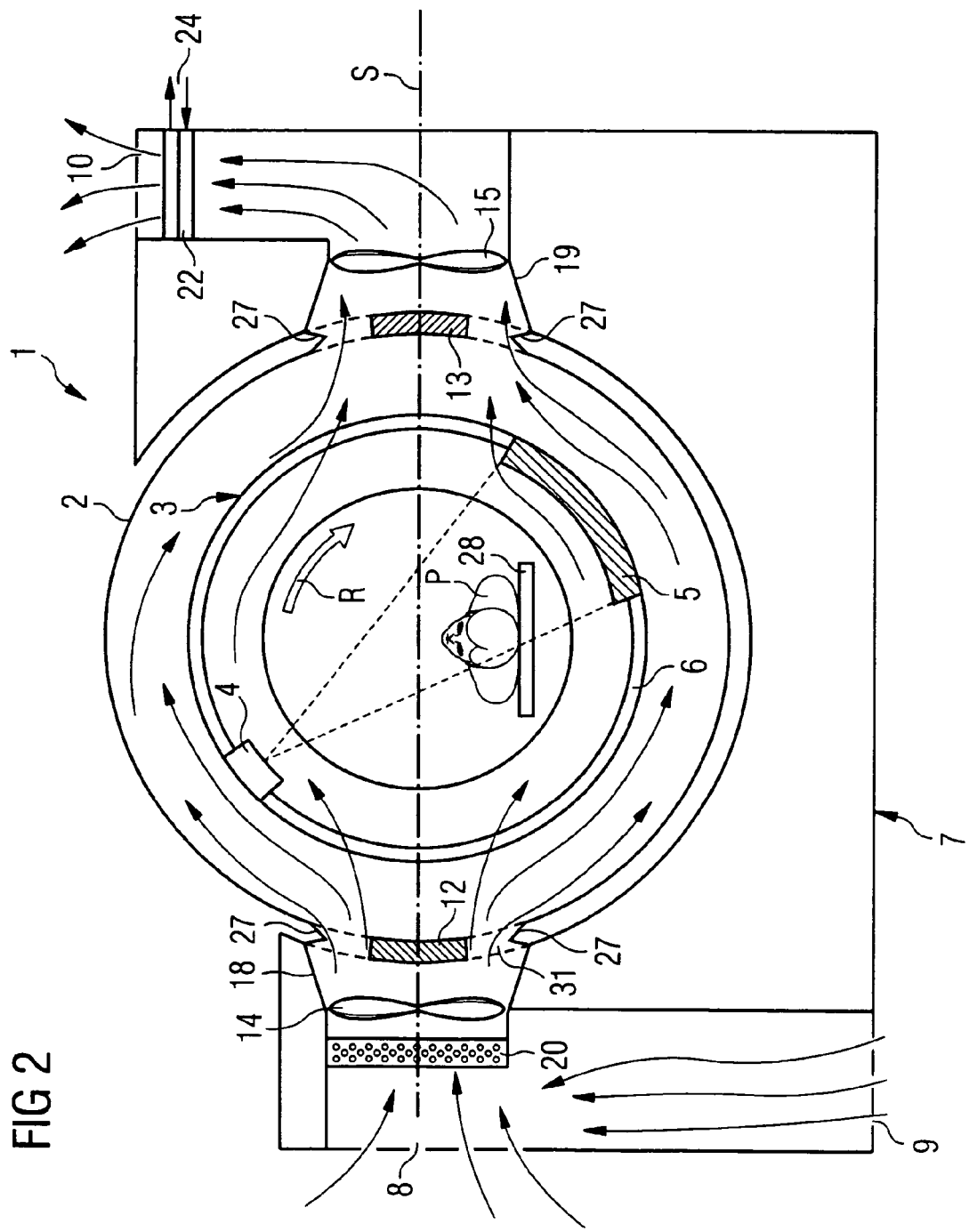
FIG. 2 is a schematic cross-sectional view of a computer tomography system with an inventive cooling system according to a second exemplary embodiment.

FIG. 2 shows an exemplary embodiment assembled similar to that of FIG. 1. However, here the cooling air W is drawn through various inflow openings 8, 9 into the gantry foot 7 by means of the blower 14. Furthermore, a heat exchanger 22 which effects a cooling of the heated air flow W is also additionally located here in the region of the second blower 15. The air cooled in this case can thus escape into the patient examination space via the outflow openings 10 in the housing of the gantry foot 7 without stressing an existing climate system.

Instead of flow-through openings in the bearings themselves, this exemplary embodiment of FIG. 2 furthermore comprises flow-through openings 31, 32 in the opposite surfaces in the housing of the gantry foot 7 and in the gantry housing 2 in the region of the pivot bearings 12, 13, and these openings are shown to be adjacent to the pivot bearings 12, 13. The volume of the air flow which can be directed into and removed from the gantry housing 2 is thus increased. The cooling effect of the cooling gas improves as a result of the larger cooling gas volume. The flow-through openings 31, 32 are preferably provided with annular seals running around the flow-through openings 31, 32 and extending between the gantry housing 2 and the housing of the gantry foot 7, in order to hold up the pressure of the cooling gas. They can be, for example, bellows-type seals 27.

In this exemplary embodiment, an additional air filter 20 is mounted in front of the blower 14 (which draws in the cooling air from outside) to prevent a contamination of the gantry 3 caused by dirt particles and dust.

Figure 3:
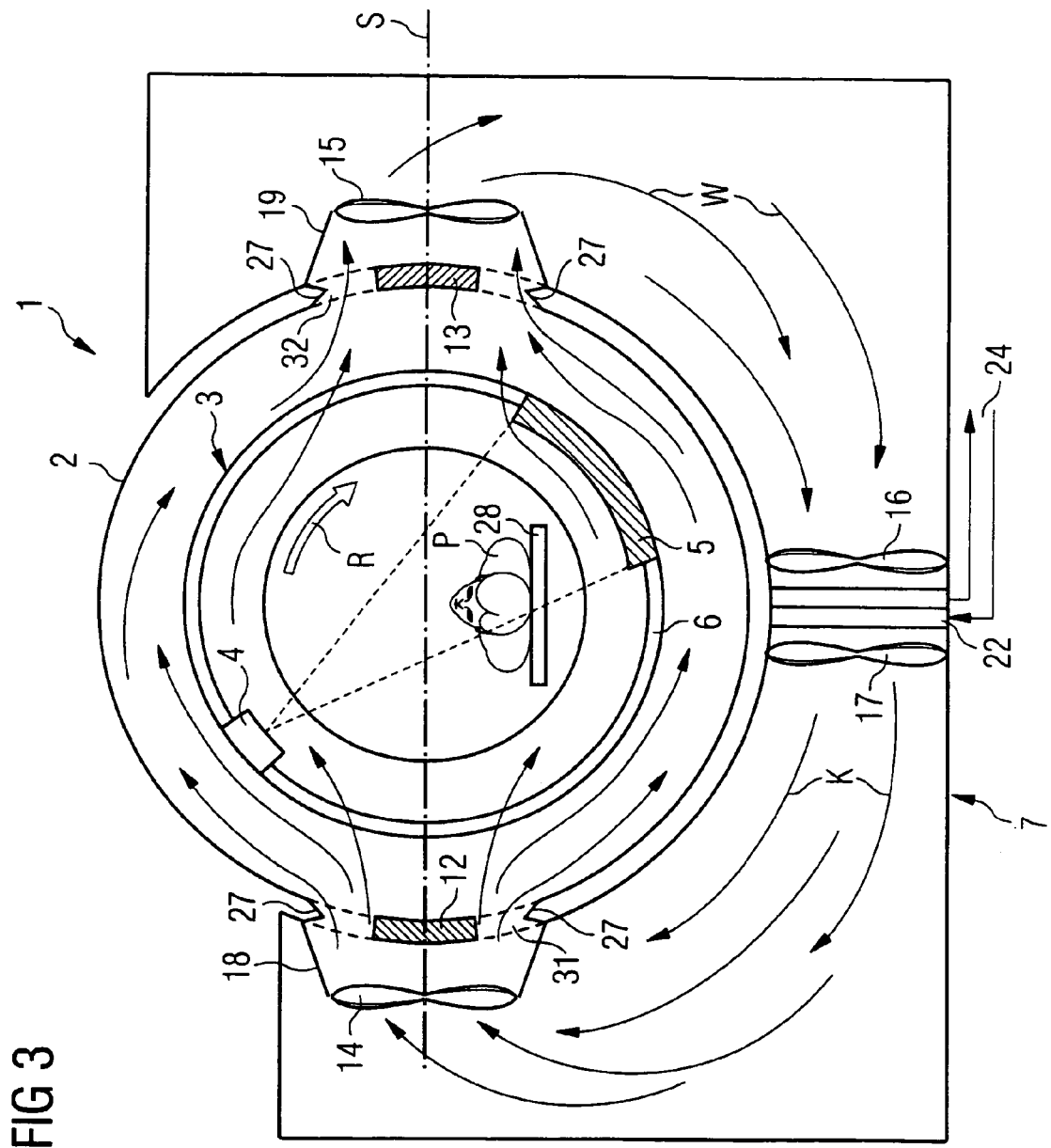
FIG. 3 is a schematic cross-sectional view of a computer tomography system with an inventive cooling system according to a third exemplary embodiment.

FIG. 3 shows another exemplary embodiment with a closed cooling gas circuit. Here as well, a cold cooling gas flow K is blown by means of a blower 14 into the gantry housing 2 through flow-through openings 31 in the region of a pivot bearing 12. The heated cooling gas flow W is in turn exhausted by means of a blower 15 on the opposite side through flow-through openings 32 in the region of the second pivot bearing 13. In the case of the present exemplary embodiment, a heat exchanger 22 is located in the gantry foot 7. The heat exchanger 22 is connected to cooling lines 24 of a water cooling circuit. The heated cooling gas W is here drawn in at the heat exchanger 22 by a blower 16 arranged directly before the heat exchanger 22 in the flow direction. The cooled cooling gas K is then pushed again from there in the direction of the first blower 14 with another blower 17 arranged directly behind the heat exchanger 22, in order to aid the flow of the cooling gas circuit.

In particular, this exemplary embodiment offers to cool additional components arranged in the gantry foot 7 by means of the cold air flow K.

Figure 4:
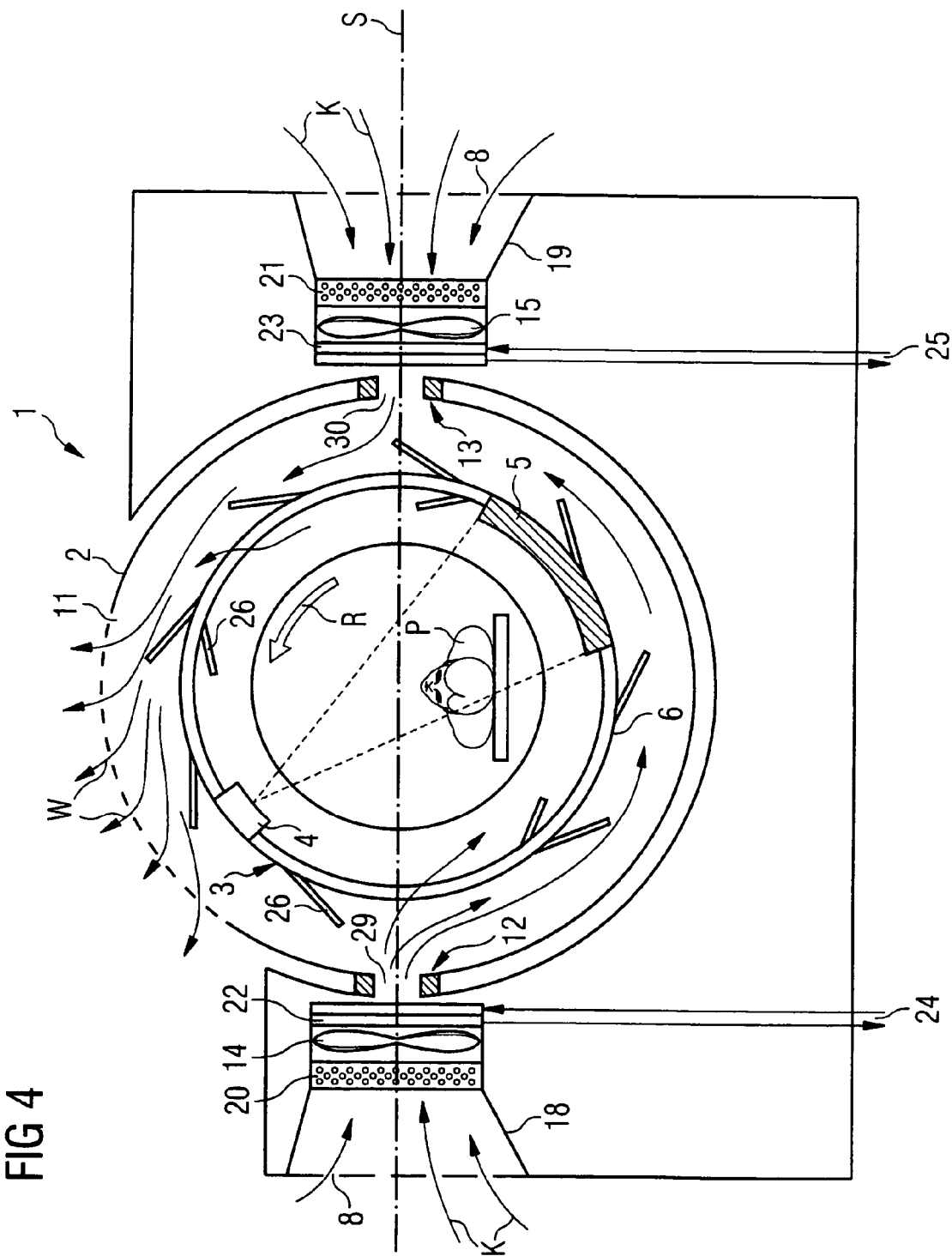
FIG. 4 is a schematic cross-sectional view of a computer tomography system with an inventive cooling system according to a fourth exemplary embodiment.

FIG. 4 shows yet another exemplary embodiment in which a cold air flow K is blown into the gantry housing 2 by means of two blowers 14, 15 through flow-through openings 29, 30 in both pivot bearings 12, 13 on the opposite sides of the gantry housing 2. The flow of the cooling air is aided as a result of the rotation of the gantry 3 and by means of flow-promoting guide vanes 26 arranged on the drum 6 inside the gantry housing 2. The heated cooling air W ultimately escapes from the gantry housing 2 through outflow openings 11 at the top of the housing. The cooling effect of the air flow is aided in that the drawn-in air is cooled before the lead-in into the gantry housing 2 by means of heat exchangers 22, 23 arranged in the region of the pivot bearings 12, 13 in the gantry foot 7. The heat exchangers 22, 23 are again connected to a cooling circuit via cooling lines 24, 25.

An increased contamination of the gantry 3 caused by dirt particles and dust is again prevented via additionally mounted air filters 20, 21 in the region of the blowers 14, 15.

The aforementioned specified arrangements of the blowers 14, 15, 16, 17 and heat exchangers 22, 23 are only to be understood as exemplary. Thus, for example, blowers and heat exchangers can be arranged as needed in the gantry foot 7 or outside of the gantry foot 7. Furthermore, additional components such as, for example, a dehumidifier can also be integrated into the air flow as needed.

Although various minor modifications may be suggested by those versed in the art, it should be understood that I wish to embody within the scope of the patent granted hereon all such modifications as reasonably and properly come within the scope of my contribution to the art.

I claim:

1. A cooling system for a gantry of a computer tomography system with an x-ray source being positioned on a gantry mounted for rotation around a rotational axis in a gantry housing which is mounted on a stationary part by at least one bearing allowing tilting of said gantry relative to said stationary part, the cooling system comprising a cooling gas supply device for directing a cooling gas flow in the region of the at least one bearing between the gantry housing and the stationary part.

2. A cooling system according to claim 1, wherein the gantry housing is mounted for pivotable movement on a pivot axis by means of two coaxial pivot bearings provided on opposite sides of the stationary part of the computer tomography system, the gas supply device creating a flow of cooling gas into the gantry housing in the region of the first of the two pivot bearings, through the gantry housing and out from the gantry housing in the region of the second of the two pivot bearings into the stationary part.

3. A cooling system according to claim 2, wherein the cooling gas flow is a closed cooling gas flow circuit.

4. A cooling system according to claim 1, which includes an outflow opening in the stationary part of the computer tomography system through which the cooling gas flows out of the stationary part after flowing through the gantry housing.

5. A cooling system according to claim 1, wherein the gantry housing is positioned so that it can be pivoted on a pivot axis by means of two coaxial pivot bearings on opposite sides of the stationary part of the tomography system, the cooling gas supply device creating a cooling gas flow into the gantry housing in the region of at least one of the pivot bearings and escapes through at least one outflow opening in the gantry housing.

6. A cooling system according to claim 5, wherein the cooling system device is constructed so that the cooling gas flows into the gantry housing in the region of both pivot bearings.

7. A cooling system according to claim 1, wherein the cooling gas flow comprises an air flow drawn in from outside of the computer tomography system through at least one inflow opening.

8. A cooling system according to claim 1, wherein the cooling gas supply device comprises at least one blower.

9. A cooling system according to claim 8, wherein the blower is located in the stationary part of the computer tomography system.

10. A cooling system according to claim 1, wherein at least one bearing has a flow-through opening running lengthwise through the bearing, through which the cooling gas flows between the stationary part and the gantry housing.

11. A cooling system according to claim 1, wherein the gantry housing and the housing of the stationary part have aligned flow-through openings at least in surfaces arranged adjacent to one of the bearings, through which the cooling gas flows between the stationary part and the gantry housing.

12. A cooling system according to claim 11, which includes seals mounted around the flow-through openings between the gantry housing and the stationary part.

13. A cooling system according to claim 1, which includes at least one heat exchanger arranged in the cooling gas flow to cool the cooling gas.

14. A cooling system according to claim 13, wherein the heat exchanger is arranged in the stationary part.

15. A cooling system according to claim 1, wherein guide means selected from guide surfaces and guide channels are arranged inside the gantry housing.

16. A computer tomography system comprising a stationary part, a gantry with an x-ray source being positioned in a gantry housing for rotation around a rotational axis, the gantry housing being mounted in said stationary part by at least one bearing allowing tilting of said gantry relative to said stationary part, and a cooling system including a cooling gas supply device for directing a cooling gas flow from a region of the at least one bearing between the stationary part and the gantry housing.

17. A method for cooling a gantry of a computer tomography system which has an x-ray source mounted thereon and is positioned in a gantry housing for rotation around a rotating axis in the gantry housing, said gantry housing being mounted in a stationary part of the computer tomography system by at least one bearing allowing tilting of said gantry relative to said stationary part, said method comprising creating a cooling gas flow and directing the gas flow from a region of the at least one bearing between the stationary part and the gantry housing for cooling the gantry.

18. A method according to claim 17, wherein the gantry housing is mounted so that it can be pivoted on a pivot axis by means of two coaxial pivot bearings on opposite sides of the stationary part of the computer tomography system and the method includes creating the cooling gas flow in the region of the pivot bearings into the gantry housing, through the gantry housing and then out of the gantry housing in the region of the second pivot bearing.

19. A method according to claim 17, wherein the step of directing the cooling gas flow directs the flow in a closed circuit.

20. A method according to claim 17, wherein a cooling gas flow includes directing the flow out of the computer tomography system after the flow has passed through the gantry housing.

21. A method according to claim 17, wherein the gantry housing is positioned so that it can be pivoted on a pivot axis by means of a first and second coaxial pivot bearing on opposite sides of the stationary part of the computer tomography system, the step of directing the cooling gas directs the cooling gas into the gantry housing in the region of at least one of the pivot bearings and dissipates the cooling gas into the surroundings through at least one outflow opening arranged in the gantry housing.

22. A method according to claim 17, wherein the step of directing a cooling gas includes cooling the cooling gas by directing it through at least one heat exchanger.

* * * * *